United States Patent [19]
Iosif et al.

[11] Patent Number: 5,474,179
[45] Date of Patent: Dec. 12, 1995

[54] NON-CONTACT PROTECTOR FOR MEDICAL DEVICE

[75] Inventors: Mario Iosif, Clark; Andrew Tybus, Succasunna, both of N.J.

[73] Assignee: C. R. Bard, Inc., Murray Hill, N.J.

[21] Appl. No.: 291,844

[22] Filed: Aug. 17, 1994

[51] Int. Cl.$^6$ .......................... B65D 81/06; B65D 85/30
[52] U.S. Cl. ........................ 206/363; 206/438; 206/521
[58] Field of Search .................................. 206/363, 349, 206/438, 592, 588, 521; 150/161

[56] References Cited

U.S. PATENT DOCUMENTS

| | | | |
|---|---|---|---|
| 428,277 | 5/1890 | Jarmuth . | |
| 3,339,608 | 9/1967 | Brenner | 206/349 X |
| 4,750,619 | 6/1988 | Cohen et al. | 206/438 |
| 4,872,551 | 10/1989 | Theros | 206/349 |
| 4,899,877 | 2/1990 | Kiernan | 206/349 |
| 5,115,913 | 5/1992 | Anhauser et al. . | |
| 5,193,679 | 3/1993 | White | 206/363 |
| 5,405,005 | 4/1995 | White | 206/363 |

FOREIGN PATENT DOCUMENTS 2306140   4/1975   France .................... 206/521

Primary Examiner—Bryon P. Gehman
Attorney, Agent, or Firm—Dennison, Meserole, Pollack & Scheiner

[57] ABSTRACT

A non-contact protector for a medical device, including a head portion and a generally cylindrical neck portion attached thereto. The protector comprises a top portion, a pair of opposed side portions flexibly hinged to the top portion, a pair of bottom portions, and a stabilizing means. The opposed side portions include locking means for retaining the protector in the closed position and side surfaces which are configured such that when the protector is in the closed position, the surfaces surround but do not contact the head portion.

9 Claims, 3 Drawing Sheets

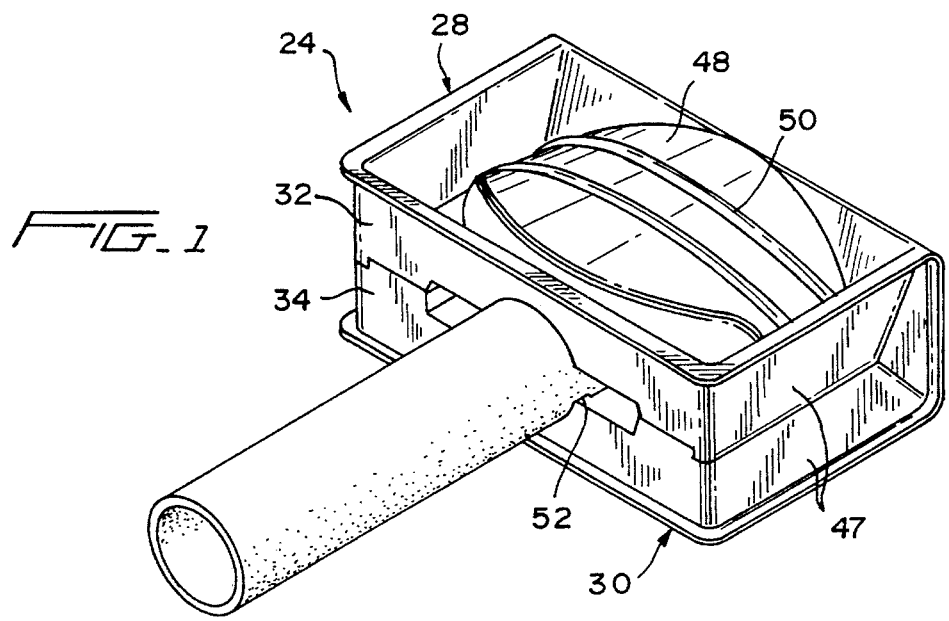
FIG_1
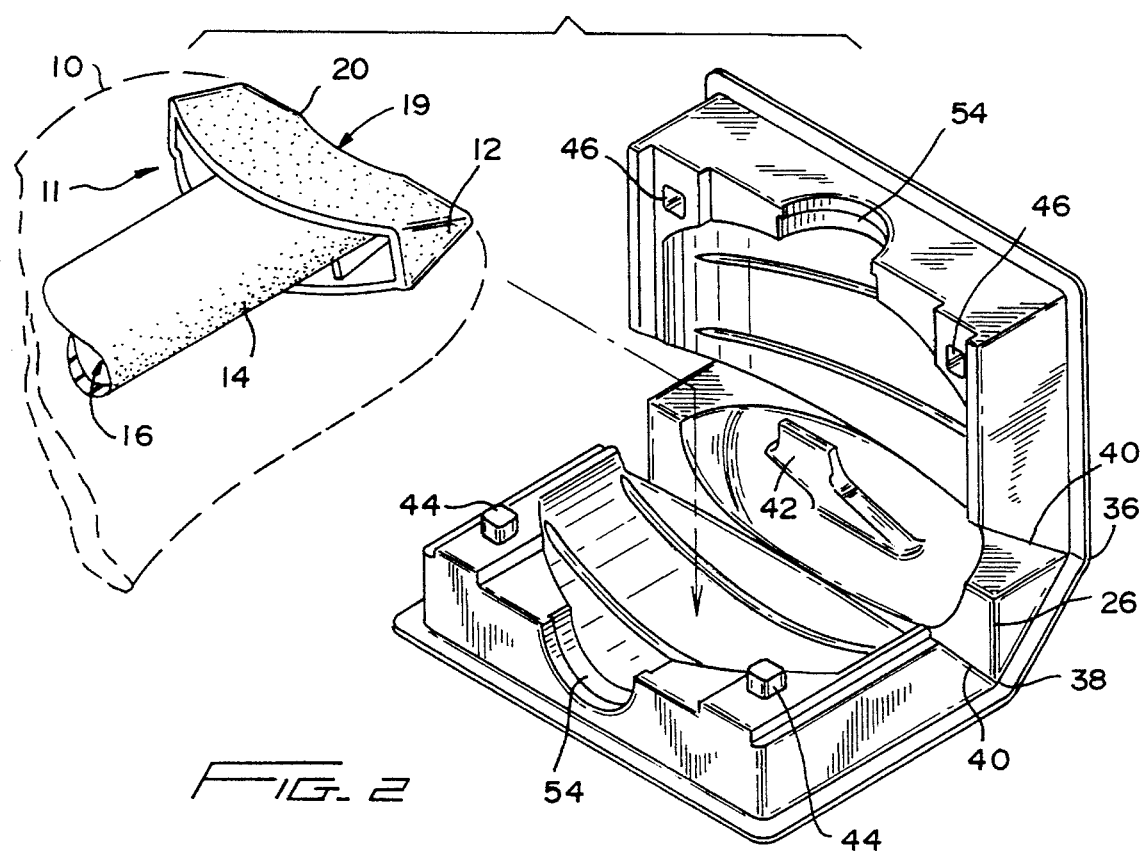
FIG_2

NON-CONTACT PROTECTOR FOR MEDICAL DEVICE

BACKGROUND OF THE INVENTION

The present invention relates to packaging of medical devices, and in particular, devices with adhesive surfaces, such as devices for collecting fecal matter from the anus of a person.

Fecal collection devices which enable collection of feces from incontinent and bedridden patients are generally known. Such devices include a gasket portion for sealing to the anus and a conduit means for permitting discharge from the anus to pass to a receptacle. One such device is disclosed in U.S. Pat. No. 4,784,656 and includes a substantially flat gasket formed of a compliant plastic material which can conform to the anal area and which is coated with an adhesive.

In another type of device which is currently available, the fecal collection device is formed from a very soft elastomeric material coated with adhesive adjacent to an opening. The device is placed using an applicator formed of a generally rigid material, with the applicator and device supplied as a unit. The applicator and device form a generally saddle-shaped gasket, the saddle shape being better designed for fitting the perianal area. The rigid applicator is removed after placement of the device.

The use of a pressure-sensitive adhesive on medical devices requires some type of protection of the adhesive surface prior to use. U.S. Pat. No. 4,784,656 discloses that the adhesive coating is covered by a protective removable release sheet made of a paper having one side coated with a release layer. This release layer is generally made of silicone, although other release materials may be used.

The use of a release sheet in contact with the adhesive surface of a medical device, and in particular, a fecal collection device has been found to be somewhat disadvantageous. The release coating has been found to present a problem with contamination of the adhesive surface, a problem which is magnified because the adhesive surface may be used in contact with sensitive areas of the human body. In addition, the interaction between the release coating and the adhesive may cause difficulties in removing the release liner.

The difficulties involved with use of a release liner have been found to increase when the adhesive contact portion is three dimensional, for example the aforementioned saddle-shape. It is far more difficult to initially apply the release sheet to the saddle-shaped contact portion and far more difficult to sustain over time reliable adherence to a three dimensional surface as opposed to a flat surface. In addition, it is more difficult to cleanly remove the release sheet from the three dimensional surface prior to actual use.

SUMMARY OF THE INVENTION

It is therefore an object of the invention to obtain a protective means for a medical device having a complex, three dimensional surface which does not involve contact between the surface and the protective means.

It is a further object of the invention to obtain protective means which will effectively protect a three dimensional adhesive surface.

These and other objects of the invention can be obtained by a non-contact protector for a medical device including a head portion with a three dimensional surface, and a neck portion. The non-contact protector comprises:

a top portion including a pair of opposed lateral edges;

a pair of opposed side portions flexibly hinged to the opposed lateral edges of the top portion, the side portions being movable between a closed position in which the protector encases the device and an open position in which the device may be removed from the protector, the opposed side portions including locking means for retaining the protector in the closed position and side surfaces which are configured such that when the protector is in the closed position, the surfaces surround but do not contact the device;

a pair of bottom portions, each bottom portion attached to a side portion opposite the top portion, the bottom portions including in the closed position an exit opening configured to surround and contact the neck portion of the device; and means for stabilizing the head and neck portions.

It is envisioned that the medical device being protected will include an adhesive coated surface of complex three dimensional shape. It is important that adhesive surfaces be protected in storage as such surfaces can attract and hold contaminants. However, it is also possible to use the non-contact protector of the invention with other devices, such as a prosthesis, e.g. a hip prosthesis, which includes a head and neck portion.

According to a preferred embodiment of the invention, the medical device being protected is a fecal collection device which includes an adhesive contact portion and a generally cylindrical neck portion with a central conduit extending through the neck portion and the adhesive contact portion. In such a case, the stabilizing means includes a stabilizing projection as part of the top portion of the device, the stabilizing projection being configured to extend into the conduit.

Where the medical device does not include a conduit, it is contemplated that the stabilizing means will include an extension of the side portions which close tightly around the neck portion of the medical device. It is also possible to provide a groove in the neck of the medical device and a corresponding tongue in the lateral portion of the non-contact protector.

The non-contact protector of the invention is preferably made as a one-piece molding from a polymer material with sufficient rigidity to be self-supporting, although complete rigidity is not required. While some deformability of the polymer is tolerated, the polymer should not be so deformable that the ordinary pressure applied in handling the device will cause the polymer to contact the surface being protected. Typical materials which can be used to form the non-contact protector are therefore polyester, polyvinyl chloride, polyethylene, polystyrene, polycarbonate and polypropylene. While the polymer is typically transparent, the polymer can also be made opaque when protection against UV or light is required.

BRIEF DESCRIPTION OF THE DRAWINGS

FIG. 1 is a perspective view of the non-contact protector and a collection device assembled;

FIG. 2 is an exploded perspective view of the non-contact protector opened and collection device;

DESCRIPTION OF THE PREFERRED EMBODIMENTS

Figure 4:
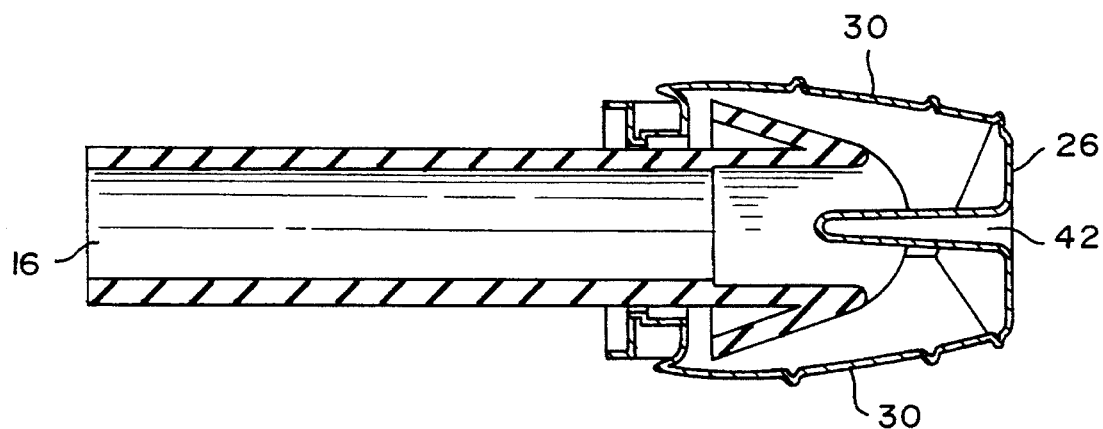
FIG. 4 is a cross-sectional view along line 4—4 of FIG. 3.
Figure 3:
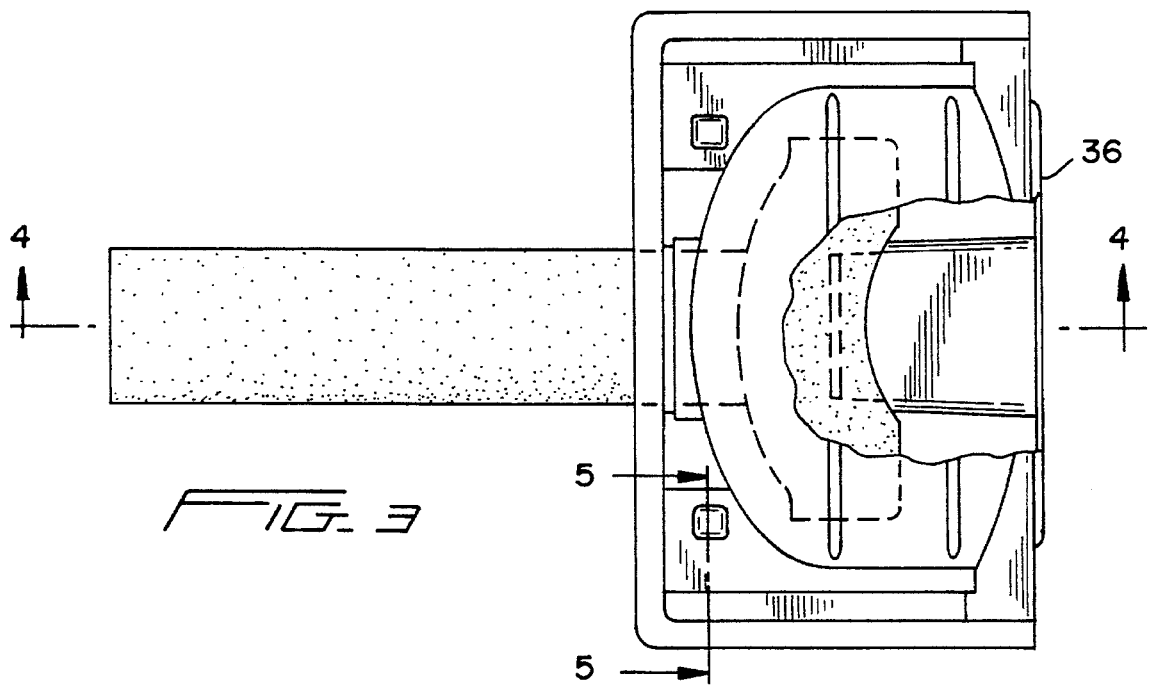
FIG. 3 is a top cut away view of the non-contact protector and collection device assembled.
Figure 5:
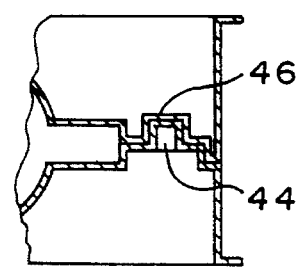
FIG. 5 is a cross-sectional view along line 5—5 of FIG. 3.

The non-contact protector of the invention is used in connection with a known fecal collection device 10 and applicator 11 shown in FIG. 2. Fecal collection device 10 may be an elastomeric rubber bag or made of another material, and is provided with an opening 19 surrounded by an adhesive coating 20. The opposite end of the device is open. The applicator 11 includes a generally saddle-shaped anal contact portion 12 and a neck portion 14, with a conduit 16 extending from opening 19 through the contact portion 12 and through the neck portion 14.

The non-contact protector is shown in detail in FIGS. 1–5. The protector 24 includes a top portion 26, side portions 28 and 30 and bottom portions 32 and 34. The top portion includes lateral edges 36 and 38 at which the side portions 28, 30 are attached to the top portion. The attachment between the top portion and the side portions is formed as an integral flexible or living hinge 40 which enables changing of the angle between the top portion and the side portions in order to open and close the protector. As shown in the Figures, this flexible hinge is formed by an appropriate reduction in thickness between the portions, although other means of forming a hinge would be equally suitable.

The top portion also includes a stabilizing projection 42 which is positioned and configured to extend into the conduit of the applicator and prevent excess movement of the protector. The side portions of the non-contact protector include locking means so that the side portions can be retained in the closed position. Shown best in FIGS. 2 and 5, the locking means include a pair of projections 44 on one of the side portions, and a pair of corresponding recesses 46 of approximately the same diameter as the projections on the other side portion. When the non-contact protector is closed around the fecal collection device and applicator, the projections frictionally mate within the recesses and releasably maintain the device in a closed position. Other locking devices known in the art are also suitable for this purpose.

In the embodiment shown in the drawings, the side walls 47 of the side portions 28, 30 are configured so that they will contact each other upon closing of the device, with intermediate bulge portions 48 domed outwardly to accommodate the shape of the applicator without contact therewith. These bulge portions 48 may include ridges 50 which provide the bulge portions added strength to prevent deformation and contact with the adhesive surface.

Other shapes for this protector can be contemplated, including a box having flat walls which are spaced such that there is no contact between the walls and the adhesive surface.

The bottom 32, 34 of the non-contact protector is shown in FIGS. 1 and 2. The bottom includes portions which are shaped such that when the protector is closed, there is an opening 52 forming a collar 54 leading to the chamber formed by the bulge portion upon closing the side portions. This collar portion 54 receives and contacts the neck portion of the fecal collection device which is not coated with adhesive. Contact with the neck portion is important in order to seal the neck portion, and thereby protect the adhesive coated portions from outside contaminants such as dust and moisture, and to also assist in stabilizing the protector on the applicator without contact with the adhesive.

Figure 6:
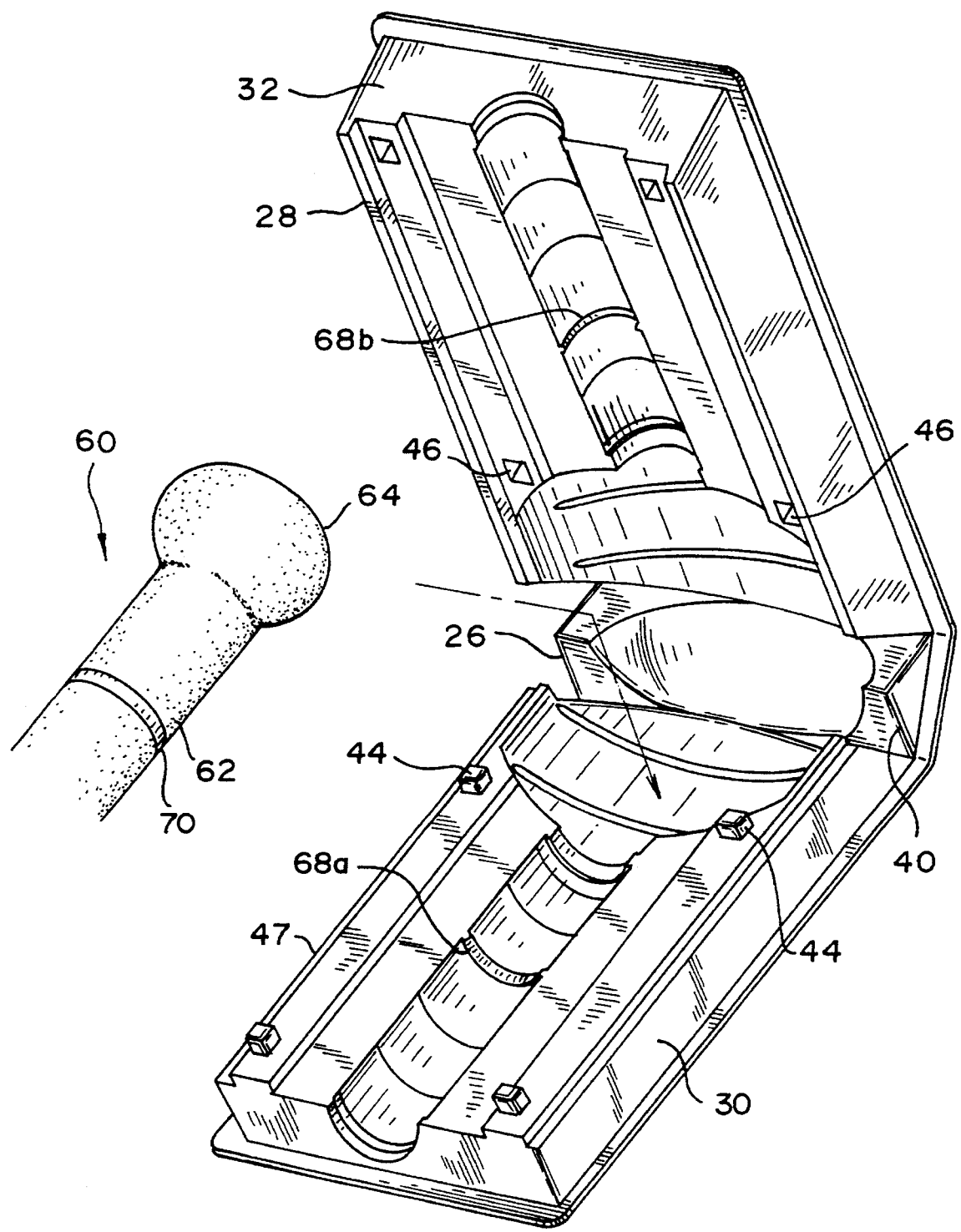
FIG. 6 is a perspective view of another embodiment of the non-contact protector for protection of a prosthesis.

Shown in FIG. 6 is another embodiment of the non-contact protector used for packaging a non-adhesive device such as a prosthetic device 60 having a neck portion 62 and head portion 64. In this embodiment, the stabilizing projection 42 has been removed, and the side walls 28 and 30 have been extended longitudinally to provide additional stabilization. In addition, top wall 26 and bottom walls 32 and 34 have been extended laterally to provide further stabilization.

Prosthetic device 60 has been formed with a groove 70 in the neck portion, the groove corresponding to tongue 68*a* and 68*b* in the non-contact protector. In this case, there would be contact between the neck portion and the protector, but there would still be no contact between the head portion and the non-contact protector.

What is claimed is:

1. A non-contact protector for a medical device, the device including a head portion and a generally cylindrical neck portion attached thereto, said non-contact protector comprising:

a top portion including a pair of opposed lateral edges;

a pair of opposed side portions flexibly hinged to the opposed lateral edges of said top portion, said side portions being movable between a closed position in which the protector encases the head portion of the medical device when retained therein and an open position in which the medical device retained therein may be removed from said protector, said opposed side portions including locking means for retaining said protector in the closed position and side surfaces which are configured such that when said protector is in the closed position with the device retained therein, said surfaces surround but do not contact the head portion;

a pair of bottom portions, each bottom portion attached to a side portion opposite the top portion, said bottom portions including in the closed position an exit opening configured to surround and contact the neck portion of the medical device when retained therein; and means for stabilizing the head and neck portions of the medical device when retained therein.

2. Protector according to claim 1, wherein the means for stabilizing includes a stabilizing projection configured to extend into a central conduit passing through the head portion and neck portion of the medical device when the device is retained in the protector.

3. Protector according to claim 1, wherein the means for stabilizing includes a longitudinal extension of said opposed side portions and a lateral extension of said top and bottom portions.

4. Protector according to claim 1, wherein said means for stabilizing includes a tongue in said side surfaces which engage a groove in the medical device, when the medical device is retained in the protector.

5. Protector according to claim 1, wherein the locking means comprises projections on one of said side portions, and corresponding recesses on the other of said side portions.

6. Protector according to claim 5, wherein said side portions include planar portions which contact each other in the closed position, and outwardly bulging portions which are configured, in the closed position, to surround the head portion.

7. Protector according to claim 6, wherein the bottom portions surrounding the exit opening are extended to form a collar portion.

8. Protector according to claim 6, wherein the bulging portions include stabilizing ridges.

9. Protector according to claim 1, wherein the bottom portions surrounding the exit opening are extended to form a collar portion.

* * * * *